United States Patent
Ludwin et al.

(10) Patent No.: US 11,877,840 B2
(45) Date of Patent: Jan. 23, 2024

(54) CATHETER LOCALIZATION USING CURRENT LOCATION COMBINED WITH MAGNETIC-FIELD SENSING

(71) Applicant: BIOSENSE WEBSTER (ISRAEL) LTD., Yokneam (IL)

(72) Inventors: Doron Moshe Ludwin, Haifa (IL); Gal Fleishon, Haifa (IL); Meir Bar-Tal, Haifa (IL); Goren Cohn, Haifa (IL); Menachem Schechter, Kiryat Ata (IL); Daniel Osadchy, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 668 days.

(21) Appl. No.: 15/991,141

(22) Filed: May 29, 2018

(65) Prior Publication Data

US 2019/0365278 A1 Dec. 5, 2019

(51) Int. Cl.
*A61B 5/06* (2006.01)
*A61B 34/20* (2016.01)
(Continued)

(52) U.S. Cl.
CPC .............. *A61B 5/063* (2013.01); *A61B 5/062* (2013.01); *A61B 5/6869* (2013.01); *A61B 34/20* (2016.02);
(Continued)

(58) Field of Classification Search
CPC ......... A61B 5/062; A61B 5/063; A61B 34/20; A61B 2034/2046; A61B 5/6852; A61B 2560/0223
See application file for complete search history.

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| EP | 2854634 A1 | 4/2015 |
| WO | WO 1996/05768 A1 | 2/1996 |
| WO | 2014/028114 A1 | 2/2014 |

OTHER PUBLICATIONS

Extended European Search Report dated Nov. 5, 2019 for the European Patent Application No. 19177011.4.
(Continued)

*Primary Examiner* — Keith M Raymond
*Assistant Examiner* — Milton Truong
(74) *Attorney, Agent, or Firm* — Volpe Koenig

(57) ABSTRACT

An apparatus includes an interface and a processor. The interface is configured for exchanging signals with: (i) a probe, which is inserted into a body of a patient and includes a flexible distal-end assembly, wherein the distal-end assembly comprises a magnetic position sensor and two or more intra-body electrodes, and, (ii) multiple body-surface electrodes attached externally to the body of the patient. The processor is configured to estimate, based on the signals exchanged with the probe, a spatial displacement of the magnetic sensor between consecutive measurements, and to estimate a position of the distal-end assembly in the body based on (i) the signals exchanged with the intra-body electrodes and the body-surface electrodes, (ii) a-priori known spatial relationships between two or more of the intra-body electrodes of the probe and (iii) the estimated spatial displacement of the magnetic sensor.

14 Claims, 3 Drawing Sheets

(51) Int. Cl.
    *A61B 5/00*     (2006.01)
    *A61B 18/14*     (2006.01)

(52) U.S. Cl.
    CPC ......... *A61B 5/6852* (2013.01); *A61B 18/1492* (2013.01); *A61B 2034/2046* (2016.02)

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,756,576 B2 | 7/2010 | Levin |
| 7,848,787 B2 | 12/2010 | Osadchy |
| 7,869,865 B2 | 1/2011 | Govari et al. |
| 8,849,393 B2 | 9/2014 | Hauck et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2007/0016007 A1 | 1/2007 | Govari et al. |
| 2007/0049817 A1 | 3/2007 | Preiss et al. |
| 2009/0030307 A1 | 1/2009 | Govari et al. |
| 2009/0138007 A1* | 5/2009 | Govari .............. A61B 1/00097 606/33 |
| 2009/0203992 A1 | 8/2009 | Govari et al. |
| 2011/0319910 A1 | 12/2011 | Roelle et al. |
| 2012/0172712 A1* | 7/2012 | Bar-Tal ................ A61B 5/0809 600/424 |
| 2012/0302869 A1* | 11/2012 | Koyrakh .............. A61B 5/065 600/409 |
| 2013/0303886 A1* | 11/2013 | Ludwin ................ A61B 5/065 600/424 |
| 2014/0095105 A1* | 4/2014 | Koyrakh ................ G01C 21/00 702/152 |
| 2016/0367168 A1 | 12/2016 | Malinin et al. |
| 2016/0367323 A1 | 12/2016 | Malinin et al. |
| 2017/0065204 A1 | 3/2017 | Ludwin et al. |
| 2019/0336035 A1* | 11/2019 | Dichterman ........... A61B 5/068 |

OTHER PUBLICATIONS

Chinese Office Action dated Jun. 6, 2022 for Chinese Patent Application No. 201910456850.5.

Japanese Office Action dated Mar. 22, 2023 for Japanese Patent Application No. 2019-099236.

\* cited by examiner

CATHETER LOCALIZATION USING CURRENT LOCATION COMBINED WITH MAGNETIC-FIELD SENSING

FIELD OF THE INVENTION

The present invention relates generally to sensing a position of an object placed within a living body, and specifically to providing corrections to impedance-based position measurements.

BACKGROUND OF THE INVENTION

Tracking the position of intrabody objects, such as insertion tubes, catheters and implants, is required for many medical procedures. For example, U.S. Patent Application Publication 2007/0016007 describes position sensing system that includes a probe adapted to be introduced into a body cavity of a subject. The probe includes a magnetic field transducer and at least one probe electrodes. A control unit is configured to measure position coordinates of the probe using the magnetic field transducer. The control unit also measures an impedance between the at least one probe electrodes and one or more points on a body surface of the subject. Using the measured position coordinates, the control unit calibrates the measured impedance.

As another example, U.S. Patent Application Publication 2014/0095105 describes an algorithm to correct and/or scale an electrical current-based coordinate system that can include the determination of one or more global transformation or interpolation functions and/or one or more local transformation functions. The global and local transformation functions can be determined by calculating a global metric tensor and a number of local metric tensors. The metric tensors can be calculated based on pre-determined and measured distances between closely-spaced sensors on a catheter.

U.S. Patent Application Publication 2011/0319910 describes systems and methods that improve control of a shapeable or steerable instrument using shape data. The method includes obtaining a plurality of localized shape data comprises using an impedance based localization system and where the shapeable instrument includes at least one sensor, where the system further includes at least one electrode where the impedance based localization system determines a voltage gradient between the sensor and the electrode. In an embodiment, a plurality of localized shape data is provided, which comprises using an electromagnetic localization system and where the shapeable instrument includes at least one electromagnetic coil.

SUMMARY OF THE INVENTION

An embodiment of the present invention that is described herein provides an apparatus including an interface and a processor. The interface is configured for exchanging signals with: (i) a probe, which is inserted into a body of a patient and includes a flexible distal-end assembly, wherein the distal-end assembly comprises a magnetic position sensor and two or more intra-body electrodes, and, (ii) multiple body-surface electrodes attached externally to the body of the patient. The processor is configured to estimate, based on the signals exchanged with the probe, a spatial displacement of the magnetic sensor between consecutive measurements, and to estimate a position of the distal-end assembly in the body based on (i) the signals exchanged with the intra-body electrodes and the body-surface electrodes, (ii) a-priori known spatial relationships between two or more of the intra-body electrodes of the probe and (iii) the estimated spatial displacement of the magnetic sensor.

In some embodiments, the processor is configured to estimate the position of the distal-end assembly by: estimating position coordinates of the intra-body electrodes based on the signals, locally-scaling the position coordinates based on the a-priori known spatial relationships, and by correcting the locally-scaled position coordinates based on the spatial displacement of the magnetic sensor.

In some embodiments, the signals received from the intra-body electrodes are indicative of at least one voltage, which is sensed by the intra-body electrodes in response to voltages applied by the body-surface electrodes.

In an embodiment, the signals received from the body-surface electrodes are indicative of currents, which are sensed by the body-surface electrodes in response to at least one current applied by the intra-body electrodes.

There is additionally provided, in accordance with an embodiment of the present invention, a method for position sensing, the method including exchanging signals with: (i) a probe, which is inserted into a body of a patient and includes a flexible distal-end assembly, wherein the distal-end assembly comprises a magnetic position sensor and two or more intra-body electrodes, and (ii) multiple body-surface electrodes attached externally to the body of the patient. Based on the signals exchanged with the probe, a spatial displacement of the magnetic sensor between consecutive measurements is estimated. A position of the distal-end assembly in the body is estimated based on (i) the signals exchanged with the intra-body electrodes and the body-surface electrodes, (ii) a-priori known spatial relationships between two or more of the intra-body electrodes of the probe and (iii) the estimated spatial displacement of the magnetic sensor.

The present invention will be more fully understood from the following detailed description of the embodiments thereof, taken together with the drawings in which:

DETAILED DESCRIPTION OF EMBODIMENTS

Overview

Figure 1:
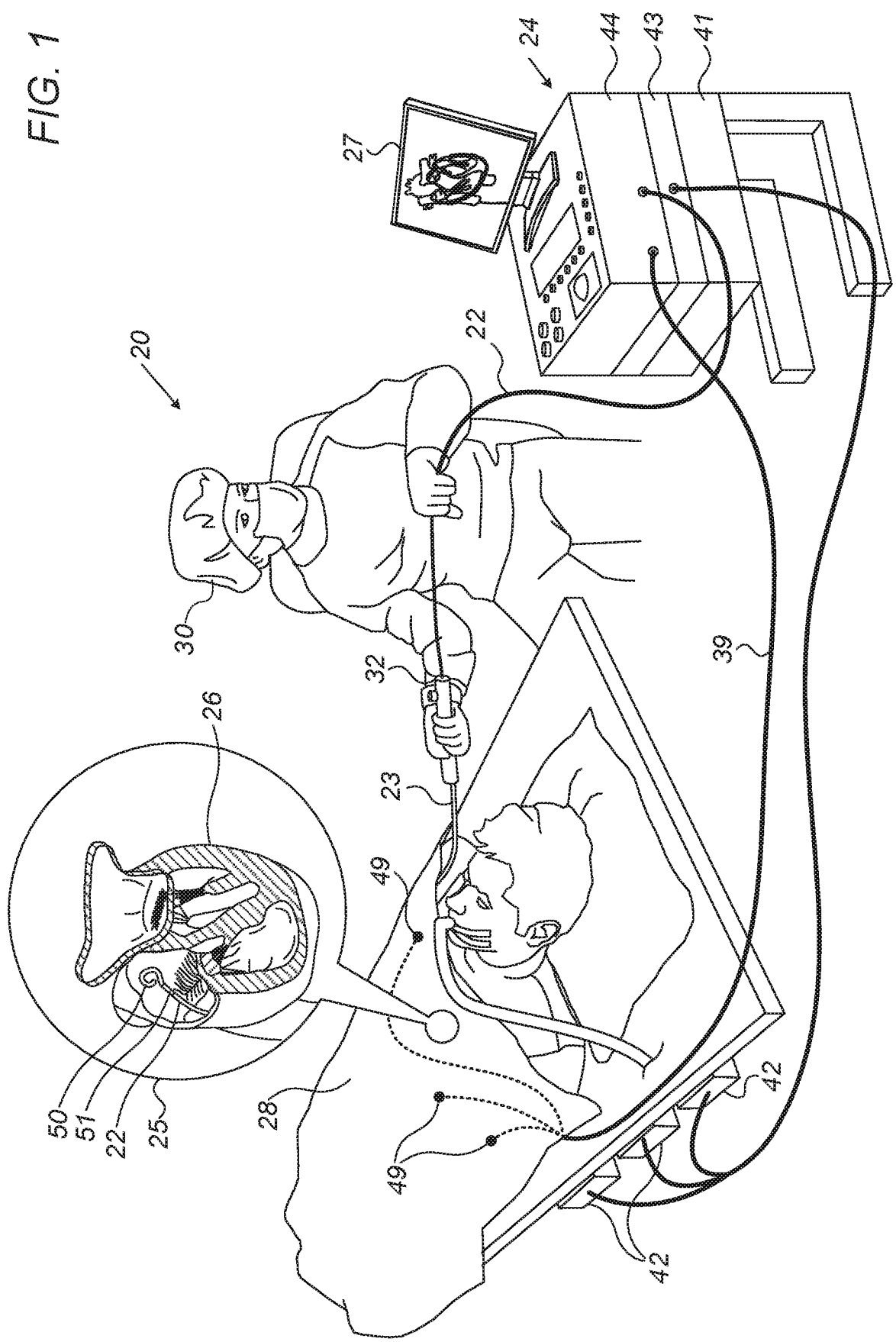
FIG. 1 is an illustration of position tracking system incorporating Active Current Location (ACL) and magnetic-sensing sub-systems, in accordance with an embodiment of the present invention.

Some medical procedures require accurate spatial mapping of an anatomy of a patient, such as that of a left atrium of a heart. Such mapping may be performed, for example, using sensing-electrodes (also referred to as intra-body electrodes) fitted to a flexible distal end assembly of a medical instrument (e.g., catheter). The sensing-electrodes are used in an impedance position tracking method. In such a method, the position of a distal end of a catheter can be estimated by measuring impedances between the sensing-electrodes and surface electrodes attached to the patient's skin. In principle, the impedance-based technique is sufficient for deriving a position of a sensing-electrode, for example in a heart. In practice, however, the resulting position accuracy is often insufficient.

In the description hereinafter, a Pure Active Current Location (PureACL) impedance-based system and technique, made by Biosense-Webster, serves as an example of impedance-based position tracking systems, while a catheter using such sensing-electrodes is named 'PureACL catheter.' The surface electrodes are named hereinafter 'ACL patches.'

In some embodiments, in order to improve the positioning accuracy of an impedance based measurement, such as that of the PureACL system, a calibration catheter is first inserted into the heart. The calibration catheter comprises a magnetic position sensor, and sensing-electrodes similar to those of the PureACL catheter. The calibration catheter is used for producing a calibration map, in which accurate position measurements by the magnetic sensor are correlated with less accurate PureACL (impedance-based) measurements.

A PureACL catheter that is subsequently inserted into the heart uses the calibration map to provide the physician a correct position of its distal end in the heart, using only sensing-electrodes (i.e., using PureACL impedance-based method).

In many practical cases, the accuracy of magnetically calibrated PureACL position sensing can be further improved using a 'local scaling' process. In some embodiments, such a process, named hereinafter 'Independent Current Location' (ICL), is applied so as to further improve the accuracy of magnetically calibrated PureACL positions. The ICL process is applicable to catheters having a plurality of sensing-electrodes disposed over their distal end. Using a known spatial relationship among two or more electrodes, e.g., one or more known distances between electrodes located up to about 1 cm from each other, possibly among other inputs, the ICL process is able to scale the relative positions of a plurality of electrodes so as to exactly fit the shape of the distal end of the PureACL catheter, finally providing highly accurate electrode positions.

The assumption used in ICL, that the actual distances between neighboring electrodes are always equal to the known distances, is valid as long as the rigidity of the distal end of the catheter is sufficient to withstand very local deformations. If this assumption is not valid, i.e., if the catheter distal end deforms by more than a permitted amount, the local scaling process does not provide the expected accuracy.

In practice, the flexible distal end assembly does deform during mapping, but on a scale of the entire assembly. Since the magnetically calibrated PureACL and ICL methods can provide accurate positions only when the distal end assembly is un-deformed, the deformation causes errors in the sensing-electrode positions derived by the magnetically calibrated PureACL and ICL method. The errors are especially large at the edges of a mapping volume, which are less fully enclosed by the surrounding ACL patches as compared with the middle of the mapped volume.

Embodiments of the present invention that are described hereinafter provide position sensing systems and methods, where a magnetic-sensor of a magnetic position-tracking system is coupled to the flexible distal end assembly. The magnetic sensor measures its own displacement between consecutive measurements (e.g., between its new measured position minus its previous measured position). The measured displacement serves as a correction to the latest PureACL and ICL measured position of the sensing electrodes. As noted above, such correction is required as a change in the sensing-electrodes positions may not be captured by the less accurate impedance based position measurement.

In some embodiments of the present invention, a magnetic sensor (i.e., a position sensor of a magnetic position-tracking system) is coupled to a base segment section of a flexible distal end assembly of a catheter. As an example, a flexible PureACL lasso catheter is provided, comprising a flexible base segment section and a spiral end section. A magnetic sensor is coupled to the base segment section.

Sensing-electrodes may be distributed over the base segment section and/or over the spiral end section. When the base segment section is deformed during a mapping procedure, actual positions of sensing-electrodes are displaced relative to the positions derived using PureACL and ICL (e.g., due to bending, deflection and/or twist of the flexible base-segment section).

Whenever the base-segment section is deformed, the magnetic sensor provides an indication of its new position (i.e., its own displacement relative to its previous indicated position) caused, for example, by the deformation. The indication is used for correcting in a consecutive manner the magnetically calibrated electrical impedance-based derived electrode positions.

In this description, the terms 'flexible PureACL catheter,' 'flexible distal-end assembly,' 'flexible base-segment section' and 'flexible catheter' are used interchangeably.

In some embodiments, the magnetic sensor provides an indication of its own displacement, relative to a position it indicated previously, with an accuracy of 1 mm in space. Adding this displacement indication to consecutive positions derived using PureACL and ICL methods yields correctly derived positions of the sensing-electrodes.

The disclosed systems and methods provide highly accurate spatial and electrophysiological mapping capabilities. These capabilities are obtained by combining compact magnetic-sensor displacement-sensing with the relatively low cost and simplicity that characterize the PureACL and ICL impedance-based position sensing. Moreover, the inherent compactness of the magnetic sensor opens the way for building compact and flexible sensing and/or ablating catheters.

System Description

FIG. 1 is an illustration of a position tracking system 20 incorporating Active Current Location (ACL) and magnetic-sensing sub-systems, in accordance with an embodiment of the present invention. System 20 is used in determining the position of a flexible PureACL catheter, such as a lasso catheter 50, seen in an inset 25 fitted at a distal end of a shaft 22. As explained above, PureACL catheter 50 incorporates sensing-electrodes (also referred to as intra-body electrodes, shown in FIG. 2) similar to those of a PureACL calibrating catheter, but need not include the same magnetic field sensors.

Physician 30 navigates lasso catheter 50 to a target location in a heart 26 of a patient 28 by manipulating shaft 22 using a manipulator 32 near the proximal end of the catheter and/or deflection from a sheath 23. Lasso catheter 50 is inserted while being folded through sheath 23, and only after sheath 23 is retracted Lasso catheter 50 regains its intended functional shape. By containing lasso catheter 50 in a folded configuration, sheath 23 also serves to minimize vascular trauma along the way to target location.

Typically, lasso catheter 50 is used for diagnostic or therapeutic treatment, such as spatially mapping the heart, and mapping respective electrical potentials in the heart prior to performing an ablation of heart tissue. Other types of catheters or other intrabody devices may alternatively be used with system 20 for other purposes, by themselves or in conjunction with other treatment devices, such as ablating catheters.

As noted above, lasso catheter 50 comprises multiple sensing-electrodes. These sensing-electrodes are connected by wires running through shaft 22 to driver circuitry in a console 24. Console 24 comprises a processor 41, typically a general-purpose computer, with suitable front end and interface circuits 44 for receiving signals from PureACL patches 49. Processor 41 is connected to PureACL patches 49, which are attached to the chest skin of patient 28, by wires running through a cable 39.

In some embodiments, processor 41 accurately determines position coordinates of the sensing-electrodes fitted at lasso catheter 50 inside heart 26. Processor 41 determines the position coordinates based on, among other inputs, measured impedances between the sensing-electrodes (on the catheter) and ACL patches 49 (i.e., using PureACL and ICL methods described above). Console 24 drives a display 27, which shows the distal end of catheter position inside the body.

The method of electrode position sensing using ACL in system 20 is implemented in various medical applications, for example in the CARTO™ system, produced by Biosense Webster Inc. (Irvine, Calif.) and is described in detail in U.S. Pat. Nos. 7,756,576, 7,869,865, and 7,848,787, whose disclosures are all incorporated herein by reference.

Console 24 further comprises a magnetic-sensing subsystem. Patient 28 is placed in a magnetic field generated by a pad containing magnetic field generator coils 42, which are driven by unit 43. The magnetic fields generated by coils 42 generate position signals in a magnetic sensor 51, which are further provided as corresponding electrical inputs to processor 41, which uses these to calculate a displacement of the sensing-electrodes due to the deformation of catheter 50, as to correct the sensing-electrodes PureACL and ICL derived positions.

In some embodiments, processor 41 is further configured to estimate a position of lasso catheter 50 (i.e., of the flexible distal-end assembly of catheter 50) in the body based on (i) electrical currents injected by the sensing-electrodes (ii) the a-priori known distances between neighboring sensing-electrodes and (iii) indication of a spatial displacement provided by magnetic sensor 51, as explained below.

In some embodiments, processor 41 is further configured to the receive position signals from a magnetic sensor 51, indicative of the position of the distal end of catheter 50 so as to calculate a displacement in space of catheter 50 due to its deformation. The method of position sensing using external magnetic fields is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description. The elements of system 20 and the methods described herein may be applied for position-sensing and/or controlling ablation using many sorts of multi-electrode catheters, such as multi-arm catheters (e.g., Pentaray®, made by Biosesne-Webster). Acquiring position signals can also be done by applying voltage gradient using ACL patch electrodes 49 or other skin attached electrodes, and measuring the potential voltage with one or more of the sensing electrodes on catheter 50. (e.g., using the Carto4® technology produced by Biosense Webster Inc. (Irvine, Calif.)). Interface circuits 44 may generally be configured to exchange signals with an intra-body probe and/or body-surface electrodes.

Catheter Localization Using Current Location Combined with Magnetic-Sensing

Figure 2:
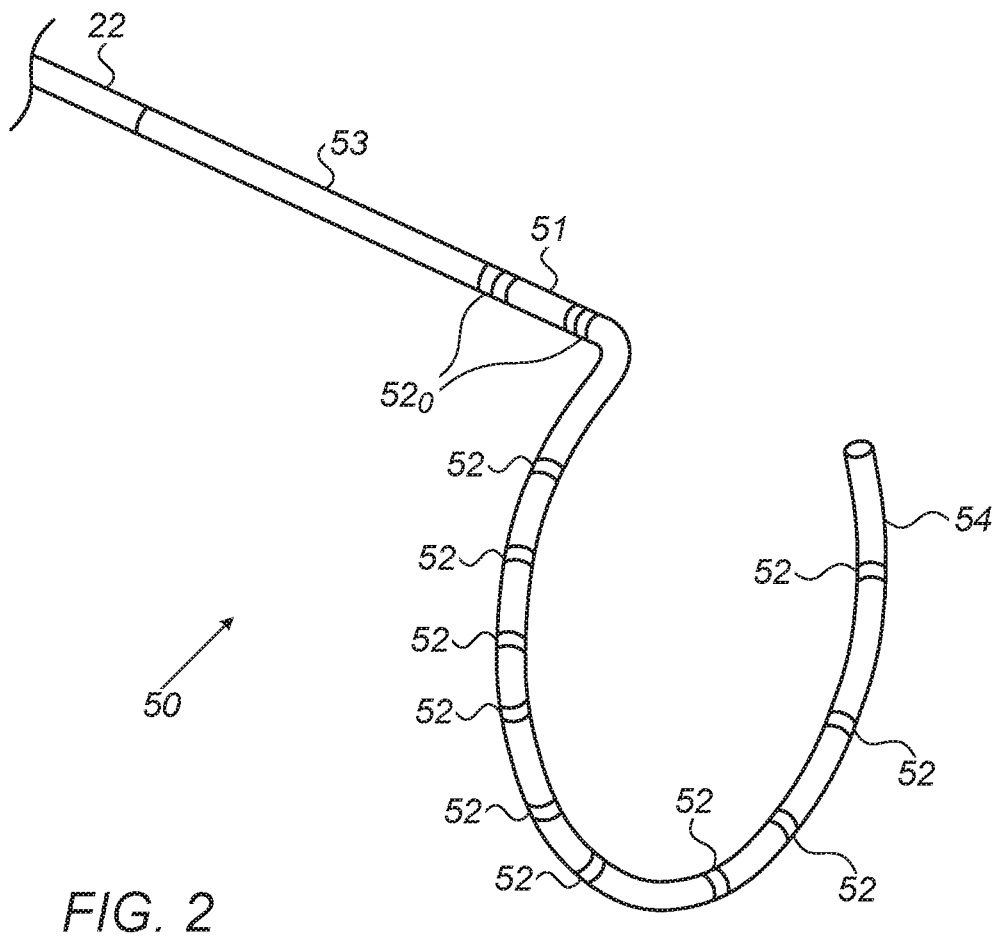
FIG. 2 is a schematic detail view showing a flexible lasso catheter comprising a magnetic sensor and multiple sensing-electrodes, in accordance with an embodiment of the present invention.

FIG. 2 is a schematic detail view showing flexible lasso catheter 50 comprising magnetic sensor 51, and multiple sensing-electrodes 52 and $52_0$, in accordance with an embodiment of the present invention. The sensing-electrodes are also referred to herein as intra-body electrodes, and the two terms are used interchangeably. As seen in FIG. 2, lasso catheter 50 is fitted at the distal end of shaft 22. Flexible lasso catheter 50 comprises a flexible base segment 53, to which magnetic sensor 51 is coupled. Two sensing electrodes $52_0$ are positioned on base segment 53, in proximity to magnetic sensor 51. Multiple sensing-electrodes 52 are circumferentially distributed over a lasso guidewire 54. In the fully expanded state of catheter 50, lasso guidewire 54 lies in a plane normal to a longitudinal axis defined by the distal end of shaft 22.

The catheter configuration described in FIG. 2 is chosen purely for the sake of conceptual clarity. In reality, lasso guidewire 54 may comprise one or more windings about the longitudinal axis defined by the distal end of shaft 22, or less than a single winding. In alternative embodiments, other flexible catheters can be fitted at the distal end of shaft 22, such as a PENTARAY® mapping catheter that comprises multiple arms. Magnetic sensor 51 may comprise one or more magnetic sensors. Only simplified sensor section is illustrated, where all other elements of magnetic sensor 51 are omitted for clarity.

Figure 3:
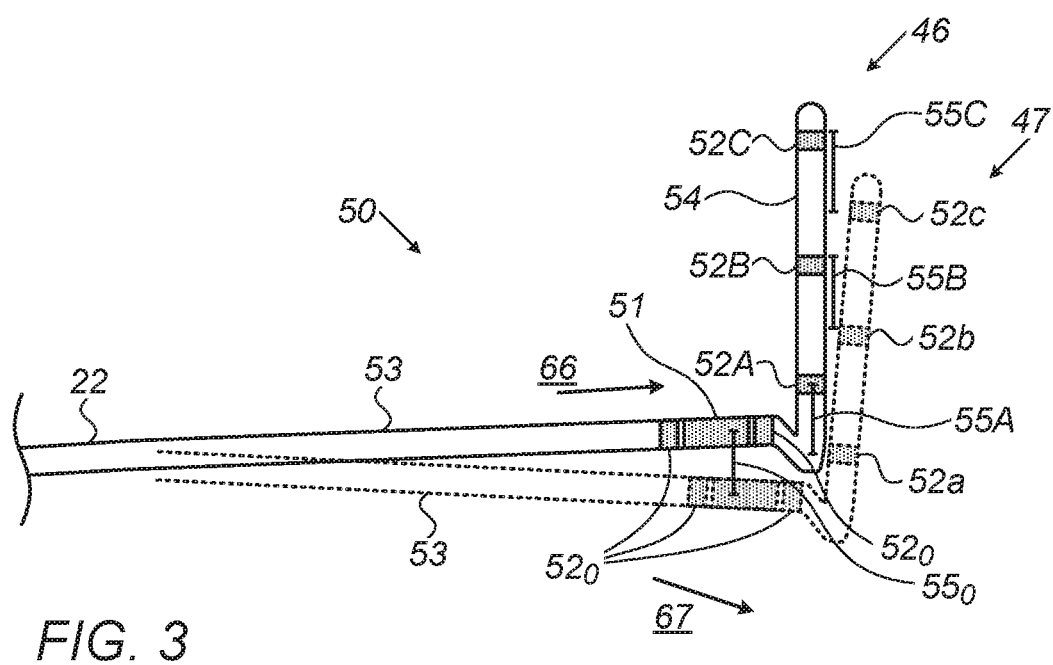
FIG. 3 is a is a schematic illustration of the flexible lasso catheter of FIG. 2, in straight and deformed states, in accordance with an embodiment of the present invention.

FIG. 3 is a is a schematic illustration of the flexible lasso catheter of FIG. 2, in straight and deformed states, in accordance with an embodiment of the present invention.

Base segment 53 of lasso catheter 50 is seen in an un-deformed state 46, and also in a deformed state 47. States 46 and 47 exemplify two consecutive states at which electrodes 52 positions are measured. When lasso base segment 53 is un-deformed, its un-deformed-direction 66 is parallel to that of the longitudinal axis defined by the distal end of shaft 22. When base segment 53 is deformed, base segment 53 (and with it lasso guidewire 54) points at a different direction, a deformed-direction 67.

As FIG. 3 shows, the deformation of base segment 53 changes the location of magnetic sensor by a displacement $55_0$. The positions of sensing-electrodes $52_0$, change as well by essentially the same displacement $55_0$. Attempting deriving deformed-direction 67 without using the disclosed technique is possible, for example, by applying PureACL and ICL methods on signals from electrodes $52_0$ on a base-segment 53. Yet the resulting positions are only accurate to about 7 mm at the edges of a mapping volume. Using embodiments of the present invention improves the accuracy at the edges of a mapped volume to about 1 mm as explained below.

The positions of sensing-electrodes 52A, 52B and 52C also change (to a good approximation) by displacement $55_0$, to positions 52a, 52b and 52c, respectively. Thus, displacement $55_0$ serves as a correct measure of displacements 55A, 55B and 55C, which characterize the majority of position change that electrodes 52A, 52B and 52C experience as a result of the exemplified deformation.

The above change in sensing electrodes positions between lasso states 46 and 47 may not be captured by the less accurate impedance based position measurement of PureACL and ICL. To correct the positions, displacement $55_0$ is measured by magnetic sensor 51. Note that in the same manner, magnetic sensor 51 will indicate an opposite displacement, $-55_0$, when a deformed state like state 47 shifts to an un-deformed state like state 46. Using displacement $55_0$ as an input, processor 41 can verify the correctness of electrode positions or correct the less accurately measured position of the flexible distal-end assembly (derived by PureACL and ICL).

The specific type of deformation of base segment 53 shown in FIG. 3 is a deflection within a plane. This deformation is depicted purely by way of example. In general, the deformation of base segment 53 of lasso catheter 50 may comprise any deformation in space, e.g., a combination of bending and/or deflection (relative to the longitudinal axis) and twist (about the longitudinal axis).

Magnetic sensor 51 is configured to provide an indication of the deformation of base segment 53. The indication is used by processor 41 to calculate a general displacement $55_0$ in space.

In an embodiment, lasso catheter 50 deforms within a certain plane in space (e.g., the deformation shown in FIG. 3). This example form of bending may occur, for example, due to the catheter structure (e.g., rigidity properties of base segment 53), or due to the nature of the anatomy being probed. In such cases the measurement of deformation is essentially one dimensional and a simplified magnetic sensor may be fitted and/or a simplified magnetic sensing method be employed.

Figure 4:
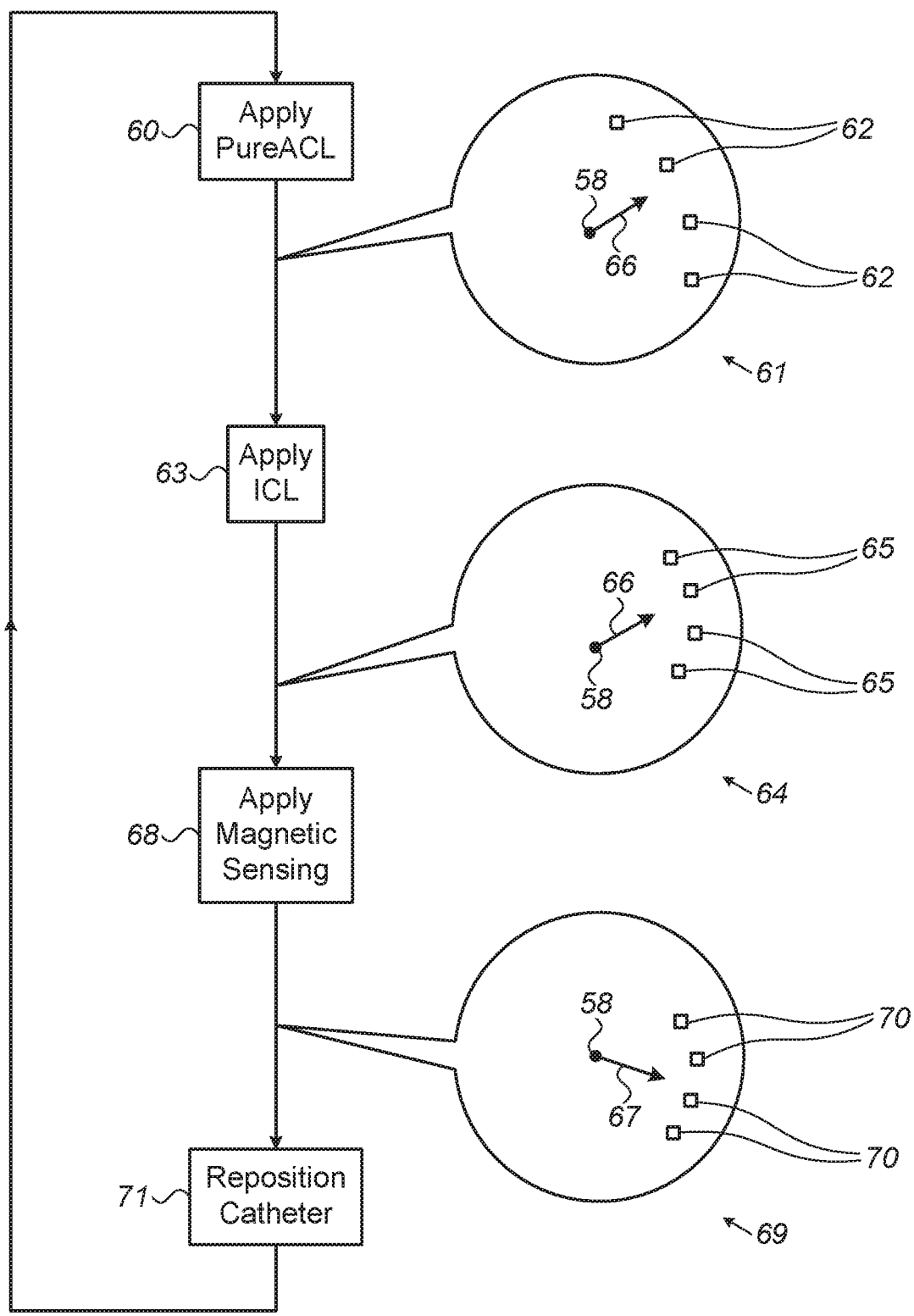
FIG. 4 is a flow chart that schematically illustrates a method for accurately mapping a cavity in the body, in accordance with an embodiment of the present invention.

FIG. 4 is a flow chart that schematically illustrates a method for accurately mapping a cavity in the body, e.g., a cardiac chamber, in accordance with an embodiment of the present invention. FIG. 4 may exemplify the position measurement of sensing electrodes 52 in deformed state 47.

At the start of the mapping procedure, processor 41 calculates positions 62 of sensing-electrodes 52, at a PureACL step 60. The positions are calculated at a given body location relative to an arbitrary origin 58, shown in inset 61. The measurement seems insensitive to the deformation of lasso catheter 50, as calculated electrode positions 62 spread about the previous un-deformed direction 66 (i.e., about electrode positions of un-deformed state 46) relative to origin 58.

Next, processor 41 calculates a local scaling factor for electrodes positions using an ICL local scaling process, at an ICL step 63. The result is shown in an inset 64, where now derived positions 65 of sensing-electrodes are distributed more compactly about un-deformed direction 66 relative to arbitrary origin 58. The spatial distribution is now correct, reflecting the local distribution of electrodes 52 on lasso 50, but electrodes positions 65 are still inaccurate compared with their real positions. Namely, the impedance based measurements were not sensitive to the deformation of the flexible distal-end assembly of lasso catheter 50.

To correct such errors, magnetic sensor 51 provides the displacement that the flexible distal-end assembly goes between subsequent measurements, i.e., between its position in state 46, and its current measured position at state 47. The change of position that magnetic sensor measures is given as displacement $55_0$, at a magnetic sensing step 68. Processor 41 corrects electrodes positions 65 by adding displacement $55_0$. As seen in an inset 69, the resulting calculated electrode positions 70 are now correctly derived to spread about the magnetically measured deformed direction 67 relative to arbitrary origin 58 (In the exemplified deformation in FIG. 3, electrode positions 70 are corrected by being shifted downwards by distance $55_0$ relative to electrode positions 65).

As physician 30 moves lasso catheter to a new position in the cavity, at a repositioning step 71, the procedure repeats itself, looping back to ACL step 60, until physician 30 received the full mapping of a cavity, for example that of a left atrium of a heart.

The example flow chart shown in FIG. 4 is chosen purely for the sake of conceptual clarity. In alternative embodiments, the order of steps may change (e.g., ACL and magnetic sensing steps may occur in parallel), and additional steps may be used, such as magnetic sensing of catheter position. The ICL method was scarcely presented, for sake of clarity. More algorithmic steps than presented are usually included in the ICL method. For example, the actual position may be determined by the ICL method by averaging the local scaling factors for each of the body voxels that the catheter has traversed nearby.

Although the embodiments described herein mainly address cardiac applications, the methods and systems described herein can also be used in other applications, such as in gastroenterology, otolaryngology and neurology.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. An apparatus, comprising:
an interface circuit for exchanging signals with:
a lasso catheter, which is inserted into a body of a patient and comprises a flexible distal-end assembly, wherein the distal-end assembly comprises a base segment with a magnetic position sensor, two or more first intra-body electrodes, and a lasso guidewire including a plurality of second intra-body electrodes, wherein the base segment is attached to the lasso guidewire; and multiple body-surface electrodes attached externally to the body of the patient; and a processor configured to estimate, based on the signals exchanged with the lasso catheter, a spatial displacement of the magnetic sensor between consecutive measurements including an original state of the magnetic position sensor and a displaced state of the magnetic position sensor, estimate a position of the distal-end assembly in the body based on (i) the signals exchanged with the plurality of second intra-body electrodes and the body-surface electrodes, (ii) a-priori known spatial relationships between neighboring electrodes of the two or more first intra-body electrodes and (iii) the estimated spatial displacement of the magnetic sensor, derive positions of the plurality of second intra-body electrodes based on a local scaling factor to obtain a spatial distribution of the plurality of second intra-body electrodes, and correct the derived positions using the displaced state to obtain corrected electrode positions.

2. The apparatus according to claim 1, wherein the processor is configured to estimate the position of the distal-end assembly by:

estimating position coordinates of the plurality of second intra-body electrodes based on the signals;

locally-scaling the position coordinates based on the a-priori known spatial relationships; and correcting the locally-scaled position coordinates based on the spatial displacement of the magnetic sensor.

3. The apparatus according to claim 1, wherein the signals received from the plurality of second intra-body electrodes are indicative of at least one voltage, which is sensed by the plurality of second intra-body electrodes in response to voltages applied by the body-surface electrodes.

4. The apparatus according to claim 1, wherein the signals received from the body-surface electrodes are indicative of currents, which are sensed by the body-surface electrodes in response to at least one current applied by the plurality of second intra-body electrodes.

5. A method for position sensing, comprising: exchanging signals with:

a lasso catheter, which is inserted into a body of a patient and comprises a flexible distal-end assembly, wherein the distal-end assembly comprises a base segment with a magnetic position sensor, two or more first intra-body electrodes, and a lasso guidewire including a plurality of second intra-body electrodes, wherein the base segment is attached to the lasso guidewire; and multiple body-surface electrodes attached externally to the body of the patient;

based on the signals exchanged with the lasso catheter, estimating a spatial displacement of the magnetic sensor between consecutive measurements including an original state of the magnetic position sensor and a displaced state of the magnetic position sensor;

estimating a position of the distal-end assembly in the body based on (i) the signals exchanged with the plurality of second intra-body electrodes and the body-surface electrodes, (ii) a-priori known spatial relationships between neighboring electrodes of the two or more first intra-body electrodes (iii) the estimated spatial displacement of the magnetic sensor, deriving positions of the plurality of second intra-body electrodes based on a local scaling factor to obtain a spatial distribution of the plurality of second intra-body electrodes, and correcting the derived positions using the displaced state to obtain corrected electrode positions.

6. The method according to claim 5, wherein estimating the position of the distal-end assembly comprises:

estimating position coordinates of the plurality of second intra-body electrodes based on the signals;

locally-scaling the position coordinates based on the a-priori known spatial relationships; and correcting the locally-scaled position coordinates based on the spatial displacement of the magnetic sensor.

7. The method according to claim 5, wherein exchanging the signals comprises receiving from the plurality of second intra-body electrodes signals, which are indicative of at least one voltage that is sensed by the plurality of second intra-body electrodes in response to voltages applied by the body-surface electrodes.

8. The method to claim 5, wherein exchanging the signals comprises receiving from the body-surface electrodes signals, which are indicative of currents that are sensed by the body-surface electrodes in response to at least one current applied by the plurality of second intra-body electrodes.

9. The apparatus according to claim 1, wherein the displaced state is a state where the base segment of the magnetic position sensor is in a different direction than a direction of the magnetic position sensor in the original state.

10. The apparatus according to claim 1, wherein the original state is a state where the base segment of the magnetic position sensor is parallel to a distal-end of a shaft.

11. The method to claim 5, wherein the displaced state is a state where the base segment of the magnetic position sensor is in a different direction than a direction of the magnetic position sensor in the original state.

12. The method to claim 5, wherein the original state is a state where the base segment of the magnetic position sensor is parallel to a distal-end of a shaft.

13. The apparatus according to claim 1, wherein (ii) the a-priori known spatial relationships further include spatial relationships between neighboring electrodes of the plurality of second intra-body electrodes.

14. The apparatus according to claim 1, wherein the plurality of second intra-body electrodes are circumferentially distributed around the lasso guidewire.

* * * * *

UNITED STATES PATENT AND TRADEMARK OFFICE
CERTIFICATE OF CORRECTION

PATENT NO. : 11,877,840 B2
APPLICATION NO. : 15/991141
DATED : January 23, 2024
INVENTOR(S) : Ludwin et al.

It is certified that error appears in the above-identified patent and that said Letters Patent is hereby corrected as shown below:

In the Specification

In Column 2, Line 49, delete "is a is a" and insert -- is a --, therefor.

In Column 6, Line 53, delete "is a is a" and insert -- is a --, therefor.

In the Claims

In Column 10, Line 29, in Claim 8, delete "to" and insert -- according to --, therefor.

In Column 10, Line 42, in Claim 11, delete "to" and insert -- according to --, therefor.

In Column 10, Line 46, in Claim 12, delete "to" and insert -- according to --, therefor.

Signed and Sealed this
Eleventh Day of June, 2024

Katherine Kelly Vidal
*Director of the United States Patent and Trademark Office*